US00PP29725P2

(12) United States Plant Patent
Olesen

(10) Patent No.: US PP29,725 P2
(45) Date of Patent: Oct. 9, 2018

(54) MINIATURE ROSE PLANT NAMED 'POULPAH092'

(50) Latin Name: ***Rosa* hybrid**
Varietal Denomination: Poulpah092

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 15/731,977

(22) Filed: Sep. 5, 2017

(51) Int. Cl.
*A01H 5/02* (2018.01)

(52) U.S. Cl.
USPC ..... Plt./121

(58) Field of Classification Search
USPC ..... Plt./121
See application file for complete search history.

*Primary Examiner* — Annette H Para

(57) ABSTRACT

A new garden rose plant of the miniature class which has abundant, lavender pink flowers and attractive foliage. This new and distinct variety has shown to be uniform and stable in the resulting generations from asexual propagation.

2 Drawing Sheets

Botanical designation: *Rosa* hybrid.
Variety denomination: 'Poulpah092'.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2011 and the resulting seeds were planted in a controlled environment in Fredensborg, Denmark. The new variety, named 'Poulpah092', originated as a single seedling from the stated cross.

The new variety may be distinguished from its male pollen parent and female seed parent primarily by the following characteristics. The male pollen parent plant has near white flowers while the new variety has lavender pink flowers. The female seed parent plant has white flowers while the new variety has lavender pink flowers.

The objective of the hybridization of this rose variety was to create a new and distinct variety with unique qualities, such as:

1. Uniform and abundant lavender pink flowers;
2. Vigorous, but compact growth when propagated on its own roots;
3. Exceptional disease resistance.

This combination of qualities is not present in previously available commercial cultivars of this type, known to the inventor, and distinguish 'Poulpah092' from all other varieties of which we are aware.

As part of the rose development program, Mogens N. Olesen germinated the seeds from the aforementioned hybridization during winter of 2011 and conducted evaluations on the resulting seedlings in a controlled environment in Fredensborg, Denmark. 'Poulpah092' was selected in the spring of 2012 by the inventor as a single plant from the progeny of the aforementioned hybridization.

Asexual reproduction of 'Poulpah092' by rooted cuttings was first done by Mogens N. Olesen in the nursery in Fredensborg, Denmark in July, 2012. This initial and other subsequent asexual propagations conducted in controlled environments have demonstrated that the characteristics of 'Poulpah092' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulpah092'.

Specifically illustrated in FIG. 1 of the drawings are open flowers, peals detached, leaves and stems.

Figure 1:
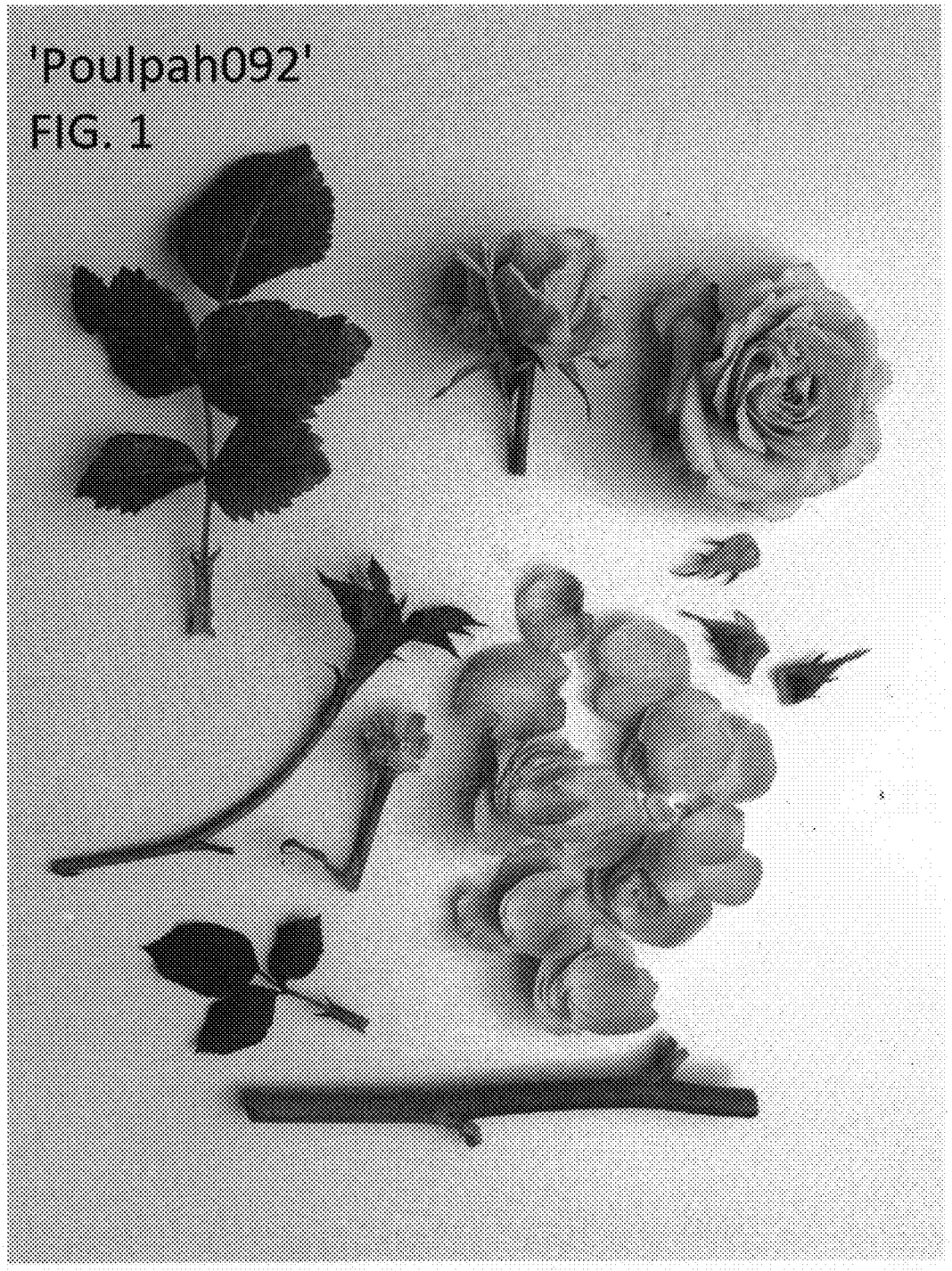
Figure 2:
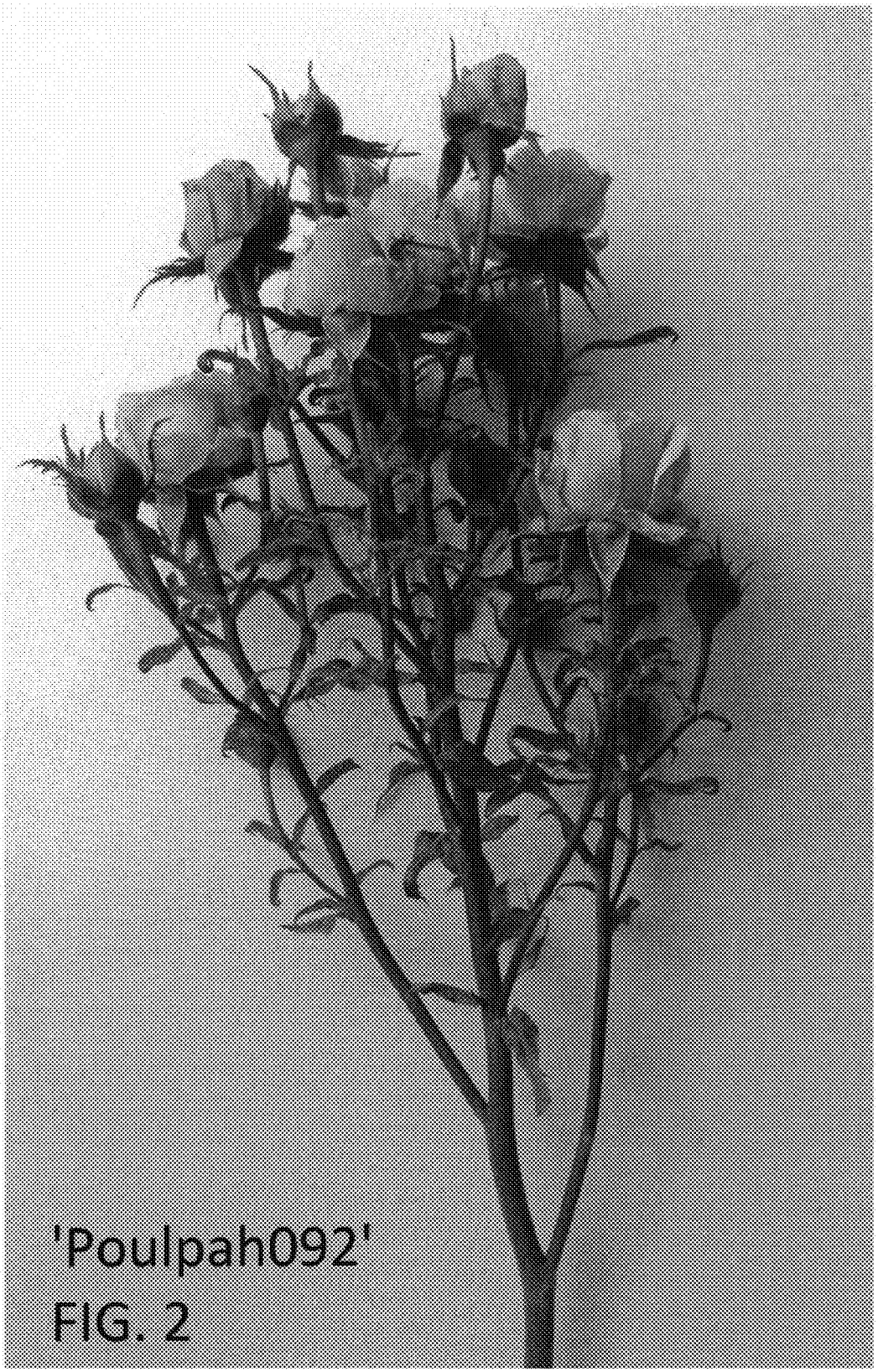

Illustrated in FIG. 2 of the drawings is a flowering branch showing flower buds, open flowers, and peduncles. Plants shown are 2 years of age.

DETAILED DESCRIPTION OF THE VARIETY

The following is a description of 'Poulpah092', as observed in its growth in a field nursery in Marion County, Oreg. Observed plants are 2 years of age, and were grown on their own roots. Color references are made using The Royal Horticultural Society (London, England) Colour Chart, 2001, except where common terms of color are used.

For a comparison, several physical characteristics of the rose variety 'Poulpah072', are compared to 'Poulpah092' in Chart 1.

CHART 1

| | 'Poulpah092' | 'Poulpah072' |
|---|---|---|
| Petal Count | 45 | 70 |
| Flower Diameter | 70 | 70 to 80 mm |
| General Tonality of Flower Color | Red-Purple Group 69A | Red Group 51C |

FLOWER AND FLOWER BUD

Blooming habit: Continuous.

Flower bud:

*Size*.—Upon opening, 23 mm in length from base of receptacle to end of bud. Bud diameter is 15 mm.

*Bud form*.—Urceolate.

*Bud color*.—As sepals divide petals are Red-Purple Group 58D.

*Sepal inner surface*.—Color: Yellow-Green Group 146D with Greyed-Red Group 181D. Surface: Pubescent.

*Sepal outer surface*.—Color: Yellow-Green Group 144A with intonations of Greyed-Purple Group 183B. Texture: Smooth.

*Sepal shape*.—Apex: Cirrhose. Base: Flat at union with receptacle.

*Sepal margin*.—Margins have moderate foliaceous appendages on three of the five sepals.

*Sepal size*.—30 mm long, 13 mm wide.

*Receptacle*.—Texture: Smooth. Size: 6 mm in height, 13 mm wide. Color: Yellow-Green Group 144A with intonations of Greyed-Red Group 181A. Shape: Funnel.

*Pedicel*.—Surface: Somewhat rough with stipitate glands. Length: 20 mm. Diameter: 3 mm on average. Color: Mostly Greyed-Purple Group 183B. Strength: Strong.

*Peduncle*.—Length: 10 to 15 cm. Diameter: About 5 mm. Color: Yellow-Green Group 144A with strong intonations of Greyed-Purple Group 183B.

*Texture*.—Smooth.

Flower bud development: Flower buds are borne in clusters of 5 to 7 flower buds per stem. Development as a panicle.

Flower bloom:

*Fragrance*.—Moderate perfume scent.

*Duration*.—The blooms have a duration on the plant of approximately 10 days. Petals do not fall cleanly away from plant after flowers have fully matured.

*Size*.—Flower diameter is 70 mm when open. Flower depth is 33 mm.

*Flower shape*.—High centered, double, with a high pointed center which is tightly closed.

*Shape of flower, side view*.—The upper portion is flat. The lower portion is flat.

Petalage: Under normal conditions, flowers have about 45 petals.

General tonality of flower: Open flowers are Red-Purple Group 69A.

Petal color:

*Upon opening, outer and inner petals*.—Upper surface: Red-Purple Group 73C. Lower surface: Red-Purple Group 73B.

*Basal petal spots, upon opening*.—Upper surface: Yellow Group 10C. Lower surface: Yellow Group 10C.

*After opening, outer and inner petals*.—Upper surface: Red-Purple Group 73C. Lower surface: Red-Purple Group 69D with other intonations of Purple Group 75C.

*Basal petal spots, after opening*.—Upper surface: Yellow Group 11D. Lower surface: Yellow Group 11D.

Petals:

*Petal reflex*.—Somewhat reflexed.

*Margin*.—Entire and uniform. Moderate undulations.

*Shape*.—Broad and elliptic. Apex shape: Rounded. Base shape: Obtuse.

*Size*.—40 mm (l)×40 mm (w).

*Texture*.—Smooth.

*Thickness*.—Average.

Petaloids:

*Size*.—18 mm (l) by 15 mm (w).

*Quantity*.—About 9.

*Shape*.—Elliptical with an acute base and rounded apex.

*Color*.—Upper surface Red-Purple Group 73C. Lower surface Red-Purple Group 69D with other intonations of Purple Group 75C. Petaloid spots are Yellow Group 11D.

Reproductive flower parts:

*Pollen*.—None observed.

*Anthers*.—Size: 2 mm in length. Color: Greyed-Yellow Group 160D. Quantity: 70 on average.

*Filaments*.—Color: Yellow Group 4D. Length: 4 mm.

*Pistils*.—Length: 10 mm. Quantity: 55 on average.

*Stigmas*.—Color: Greyed-Yellow Group 160D.

*Styles*.—Color: Green-White Group 157C.

*Location of stigmas*.—Superior in location relative to the length of the filaments and the height of the anthers.

*Hips*.—None Observed.

PLANT

Plant growth: Upright, bushy. Plants are 40 cm in height, and 35 cm wide.

Stems:

*Color of juvenile growth*.—Yellow-Green Group 144A with intonations of Greyed-Purple Group 183C.

*Color of mature growth*.—Yellow-Green Group 144A with very strong intonations of Greyed-Purple Group 183C.

*Length*.—Canes are about 30 cm from the base of the plant to the flowering portion.

*Diameter*.—About 9 mm.

*Internodes*.—On mature canes about 55 mm between nodes.

*Surface texture*.—Young wood: Smooth. Older wood: Smooth.

Long prickles: None observed.

Plant foliage:

*Compound leaf*.—140 mm (l)×85 (w).

*Quantity*.—2 leaves per 10 cm of stem on average.

*Leaf bearing angle to the stem*.—45 degrees.

*Color of juvenile foliage*.—Upper side: Greyed-Purple Group 183A. Lower side: Greyed-Purple Group 183A.

*Color of mature foliage*.—Upper side: Yellow-Green Group 146A. Lower side: Yellow-Green Group 146B.

Plant leaves and leaflets:

*Stipules*.—Size: 23 mm long, 2 mm wide. Quantity: 2 per compound leaf Shape: Linear, slightly broad based with outward extending apices. Margins: Finely serrated. Color: Yellow-Green Group 144A.

*Petiole*.—Length: 40 mm. Diameter: 2 mm. Upper surface color: Yellow-Green Group 144A. Lower surface color: Yellow-Green Group 144A.

*Rachis*.—Length: 45 mm. Upper surface color: Yellow-Green Group 144A. Lower surface color: Yellow-Green Group 144A.

*Leaflet*.—Quantity: Normally 5 leaflets. Margins: Serrated. Size: Terminal leaflets are about 55 mm long, 43 mm wide. Shape: Generally ovate. Base: Rounded. Apex: Cuspidate. Texture: Smooth. Thickness: Average. Arrangement: Odd pinnate. Venation: Reticulate. Glossiness: Not glossy.

Disease resistance: Above average resistance to powdery mildew *Sphaerotheca pannosa*, downy mildew *Peronospora sparsa*, rust *Phragmidium* sps., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant of the miniature rose class named 'Poulpah092', substantially as illustrated and described herein, due to its abundant lavender pink flowers, disease resistance, and extended period of bloom.

* * * * *

'Poulpah092'